United States Patent [19]

Edwards et al.

[11] Patent Number: 5,362,916

[45] Date of Patent: Nov. 8, 1994

[54] SYNTHESIS OF MERCAPTARYL OR HYDROXYARYL ENOL ETHER ALKALI METAL SALTS

[75] Inventors: Brooks Edwards, Cambridge; Rouh-Rong Juo, Alston, both of Mass.

[73] Assignee: Tropix, Inc., Bedford, Mass.

[21] Appl. No.: 153,791

[22] Filed: Nov. 17, 1993

Related U.S. Application Data

[63] Continuation of Ser. No. 881,140, May 11, 1992, abandoned, which is a continuation of Ser. No. 574,789, Aug. 30, 1990, abandoned, which is a continuation-in-part of Ser. No. 402,847, Sep. 6, 1989, abandoned.

[51] Int. Cl.$^5$ .................. G01N 21/76; C07C 49/167
[52] U.S. Cl. ........................................ 568/61; 568/62; 568/375; 568/667; 585/352
[58] Field of Search ............ 568/61, 62, 375, 667; 585/352

[56] References Cited

U.S. PATENT DOCUMENTS 4,956,477  9/1990  Bronstein et al. .................. 549/221

FOREIGN PATENT DOCUMENTS 0254051  1/1988  European Pat. Off. .
8800695  1/1988  WIPO .
8906226  7/1989  WIPO .

OTHER PUBLICATIONS

Wadsworth et al., Journal of the American Chemical Society, vol. 83, pp. 1733–1738, 1961.
McMurray et al., *J. Org. Chem.*, 43, 3255 (1978).
Magnus et al., *Organometallics*, 1, 553 (1982).
Wynberg et al., *Tet. Letts.*, 41, 3997 (1979).
Walker in Cudogan, Organophos. Reags. In Org. Synth., A. P., 155 (1978).
Gushurst, *J. Org. Chem.*, 53, 3397 (1988).
Horner et al., *Chem. Ber.*, 95, 581 (1962).
Wadsworth et al., *J. Am. Chem. Soc.*, 83, 1733 (1961).
Arbuzov et al., *Chem. Ber.*, 60, 291 (1927).
Burkhouse et al., *Synthesis*, 330 (1984).
Creary et al., *J. Org. Chem.*, 50, 2165 (1985).
Oh et al., *Synth. Comm.*, 16(8), 859 (1986).
Boutagy et al., *Chem. Revs.*, 74, 87 (1974).
L. A. Slotin, *Synthesis*, 737 (1977).
King et al., *Biochem. J.*, 33, 1182 (1939).
Shah et al., *Carbohydrate Res.*, 74, 105 (1979).
Feutrill et al., *Aust. J. Chem.*, 25, 1731 (1972).
Feutrill et al., *Tetrahedron Lett.*, 16, 1327 (1970).
T. W. Greene, Protective Groups in Organic Synthesis, 88 (1981).
Bhatt et al, *Synthesis*, 249 (1983).

*Primary Examiner*—José G. Dees
*Assistant Examiner*—Deborah D. Carr
*Attorney, Agent, or Firm*—David G. Conlin; Linda M. Buckley

[57] ABSTRACT

Hydroxyaryl enol ether alkali metal salts having the formula:

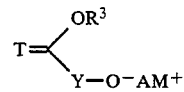

in which T is a fused, substituted or unsubstituted polycycloalkylidene group, $OR^3$ is an ether group Y is a light-emitting fluorophore-forming group which will be part of a luminescent substance formed by decomposition of a 1,2-dioxetane subsequently formed from the hydroxyaryl enol ether alkali metal salt, capable of absorbing energy to form an excited state from which it emits optically detectable energy to return to its ground state, and $AM^{30}$ is an alkali metal cation, processes for the preparation of these intermediate salts, and their use as starting materials for acylation, phosphorylation and glycosylation reactions to give intermediates reactable to give stable, water-soluble chemiluminescent 1,2-dioketames, particularly ones that are enzymatically cleavable, are disclosed.

13 Claims, No Drawings

SYNTHESIS OF MERCAPTARYL OR HYDROXYARYL ENOL ETHER ALKALI METAL SALTS

This is a continuation of copending application Ser. No. 07/881,140 filed on May 11, 1992, now abandoned, which is a continuation of copending application Ser. No. 07/574,789 filed on Aug. 30, 1990, now abandoned, which is a continuation-in-part of our U.S. patent application Ser. No. 402,847, filed Sep. 6, 1989 now abandoned.

BACKGROUND OF THE INVENTION

Our above-mentioned copending U.S. patent application, the entire content of which is incorporated by reference as though set forth herein, discloses and claims a new synthesis of stable, water-soluble chemiluminescent 1,2-dioxetanes, particularly ones that are enzymatically cleavable, substituted with stabilizing and solubilizing groups and ring-containing fluorophore moieties. The synthesis employs dialkyl 1-alkoxy-1-arylmethane phosphonate α-carbanion intermediates in the synthesis of key enol ether intermediates for the desired 1,2-dioxetane end products.

Among the 1,2-dioxetanes that can be obtained by the novel synthetic method of our above-mentioned application are those represented by the formula:

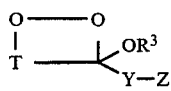
(I)

In this formula the symbol T represents a spiro-bonded stabilizing group, a gem carbon atom of which is also the 3-carbon atom of the dioxetane ring.

The most preferred stabilizing groups represented by T are fused, substituted or unsubstituted polycycloalkylidene groups, bonded to the 3-carbon atom of the dioxetane ring through a spiro linkage and having two or more fused rings, each ring having from 3 to 12 carbon atoms, inclusive, e.g., an adamant-2-ylidene group. The fused polycycloalkylidene group may additionally contain unsaturated bonds or 1,2-fused aromatic rings, or a substituted or unsubstituted alkyl group having from 1 to 12 carbon atoms, inclusive, such as methyl, ethyl, tertiary butyl, trifluoromethyl or 2-cyanoethyl, or an aryl or substituted aryl group such as carboxyphenyl, or a halogen group such as fluoro or chloro, or a heteroatom group which can be a substituted or unsubstituted alkoxy or aryloxy group having from 1 to 12 carbon atoms, inclusive, such as a methoxy, ethoxy, hydroxyethoxy, methoxyethoxy, carboxymethoxy, or polyethylethyleneoxy group, or a cyano group, a methanesulfonyl group or other electron-withdrawing group.

$OR^3$ is an ether group, prefereably a lower alkyl ether group such as a methoxy group, in which the symbol $R^3$ represents a $C_1$-$C_{20}$ unbranched or branched, substituted or unsubstituted, saturated or unsaturated alkyl group, e.g., methyl, ethyl, allyl or isobutyl; a heteroaralkyl or aralkyl (including ethylenically unsaturated aralkyl) group, e.g., benzyl or vinylbenzyl; a polynuclear (fused ring) or heteropolynuclear aralkyl group which may be further substituted, e.g., naphthylmethyl or 2-(benzothiazol-2′-yl)ethyl; a saturated or unsaturated cycloalkyl group, e.g., cyclohexyl or cyclohexenyl; a N, O, or S heteroatom containing group, e.g, 4-hydroxybutyl, methoxyethyl, ethoxyethyl or polyalkyleneoxyalkyl; or an aryl group, any of which may be fused to Y such that the emitting fragment contains a lactone ring, or an enzymatically cleavable group containing a bond cleavable by an enzyme to yield an electron-rich moiety bonded to the dioxetane ring; preferably, X is a methoxy group.

The symbol Y represents a light-emitting fluorophore-forming group, part of a luminescent substance capable of absorbing energy upon decomposition of the 1,2-dioxetane to form an excited state from which it emits optically detectable energy to return to its ground state. Preferred are phenyl, biphenyl, 9,10-dihydrophenanthryl, naphthyl, anthryl, pyridyl, quinolinyl, isoquinolinyl, phenanthryl, pyrenyl, coumarinyl, carbostyryl, acridinyl, dibenzosuberyl, phthalyl, or derivatives thereof.

The symbol Z represents hydrogen (in which case the dioxetane can be thermally cleaved by a rupture of the oxygen-oxygen bond), a chemically cleavable group such as a hydroxyl group, an alkanoyloxy or aroyloxy ester group, a silyloxy group, or an enzyme-cleavable group containing a bond cleavable by an enzyme to yield an electron-rich moiety bonded to the dioxetane ring, e.g., a bond which, when cleaved, yields a Y-appended oxygen anion, a sulfur anion, an amino or substituted amino group, or a nitrogen anion, and particularly an amido anion such as a sulfonamido anion.

One or more of the groups represented by the symbols T, $R^3$ and Z can also include a substituent which enhances the water solubility of the 1,2-dioxetane, such as a carboxy or carboxy-containing group, e.g., a carboxymethoxy group, a sulfonic acid group, e.g., an aryl sulfonic acid group, or carboxylic acid or sulfonate salts, or a quaternary amino salt group, e.g., trimethylammonium chloride, with any appropriate counterion.

Enzymatically cleavable 1,2-dioxetanes can be cleaved using an enzyme such as an alkaline phosphatase that will cleave a bond in, for example, a Z substituent such as a phosphate monoester group, to produce a Y oxyanion of lower oxidation potential that will, in turn, destabilize the dioxetane and cleave its ring oxygen-oxygen bond. Alternatively, catalytic antibodies may be used to cleave the Z substituent. Destabilization can also be accomplished by using an enzyme such as an oxido-reductase enzyme that will cleave the oxygen-oxygen bond directly.

Z in formula I above can also be an enzyme-cleavable alkanoyloxy group, e.g., an acetate ester group, an oxacarboxylate group, or an oxaalkoxycarbonyl group, a 1-phospho-2,3-diacylglyceride group, a 1-thio-D-glucoside group, an adenosine triphosphate analog group, adenosine diphosphate analog group, adenosine monophosphate analog group, adenosine analog group, α-D-galactoside group, β-D-galactoside group, α-D-glucoside group, β-D-glucoside group, α-D-mannoside group, β-D-mannoside group, β-D-fructofuranoside group, β-D-glucosiduronate group, an amide group, a p-toluene sulfonyl-L-arginine ester group, or a p-toluene sulfonyl-L-arginine amide group.

The new synthetic method for producing 1,2-dioxetanes disclosed and claimed in our copending application Ser. No. 402,847 can be illustrated in part by the following reaction sequence leading to the preparation of 1,2-dioxetanes having both an alkoxy (or aryloxy) and an aryl substituent at the 4-position, the latter (illustrated here as an aryl Y substituent) itself being substituted by one or more $X^1$ groups, these $X^1$ substituents being ortho, meta, or para to each other. Groups $R^2$ and $X^1$ need not be static during the reaction sequence, but may be interconverted under conditions which are compatible with structural considerations at each stage.

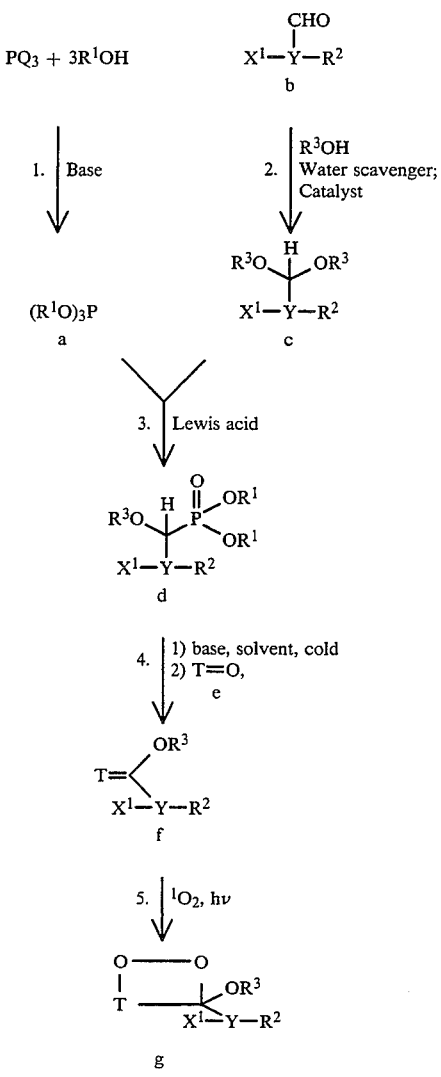

In these formulas: T is as described above for Formula I. Any Q can be, independently, a halogen, e.g., chlorine or bromine, or $OR^1$; $R^1$ can be, independently, a trialkylsilyl group, or an alkyl group, the alkyl group in either case having from 1 to about 12 carbon atoms, and preferably methyl, ethyl, propyl, or butyl; $R^2$ can be a hydroxyl group, an ($ER^4$) group, i.e., an ether ($OR^4$) or a thioether ($SR^4$) group wherein $R^4$ is a substituted or unsubstituted alkenyl, alkyl or aralkyl group having up to 20 carbon atoms such as methyl, allyl, benzyl, or o-nitrobenzyl. $R^2$ can also be an acyloxy group such as acetoxy, pivaloyloxy, or mesitoyloxy, a halogen atom, e.g., chlorine or bromine, a nitro group, an amino group, a mono or di(lower)alkylamino group or its acid salt wherein each lower alkyl substituent contains up to 7 carbon atoms, such as methyl, ethyl, or butyl, where any or all of these lower alkyl groups may be bonded to Y to generate one or more fused rings, or a $NHSO_2R^5$ group wherein $R^5$ is methyl, tolyl, or trifluoromethyl. $R^2$ can also be a substituted aryl, heteroaryl, or -styrenyl group containing up to 20 carbon atoms such as a 4-methoxyphenyl or 6-methoxybenzthiazol-2-yl group.

$R^3$ can be a substituted or unsubstituted alkyl, aralkyl, or heteroaralkyl group having up to 20 carbon atoms such as methyl, trifluoroethyl, or benzyl, an aryl or heteroaryl group having up to 14 carbon atoms which may be further substituted, e.g., a 4-chlorophenyl group, a (lower)alkyl-$OSiX_3$ group in which the lower alkyl group contains up to 6 carbon atoms, such as ethyl, propyl, or hexyl, and any X is independently methyl, phenyl, or t-butyl, an alkoxy(lower)alkyl group such as ethoxyethyl or ethoxypropyl, a hydroxy(lower)alkyl group having up to 6 carbon atoms such as hydroxyethyl, hydroxybutyl or hydroxyhexyl, or an amino(lower)alkyl or mono or di(lower)alkylaminoalkyl group where each lower alkyl group contains up to 7 carbon atoms, such as methyl, ethyl, or benzyl.

$X^1$ can be hydrogen or a substituted or unsubstituted aryl, aralkyl, heteroaryl, or heteroaralkyl group having up to 20 carbon atoms such as a 4,5-diphenyloxazol-2-yl, benzoxazol-2-yl or 3,6-dimethoxy-9-hydroxyxanthen-9-yl group, an allyl group, a hydroxy(lower)alkyl group having up to 6 carbon atoms such as hydroxymethyl, hydroxyethyl or hydroxypropyl, a (lower)alkyl-$OSiX_3$ group wherein the alkyl and X radicals are as defined above, an ether ($OR^4$) or a thioether ($SR^4$) wherein $R^4$ is as defined above, an $SO_2R^6$ group wherein $R^6$ is methyl phenyl or $NHC_6H_5$, a substituted or unsubstituted alkyl group containing up to 7 carbon atoms such as methyl, trifluoromethyl or t-butyl, a nitro group, a cyano group, an aldehydic function or its oxime or dimethylhydrazone, an alkyl halide group having up to 6 carbon atoms whose halo substituent is preferably chlorine or bromine, a halogen atom, a hydroxyl group, a carboxyl group or a salt, ester or hydrazide derivative thereof, a tri-substituted silicon-based group such as a trimethylsilyl group, or a phosphoryloxy (phosphate monoester) group.

Step 1 of the foregoing reaction sequence involves the formation of a tertiary phosphorous acid alkyl ester from a phosphorous trihalide, e.g., phosphorous trichloride or dialkylchlorophosphite, and an alcohol, e.g., a short chain alkyl alcohol, preferably one having up to 7 carbon atoms such as methanol, ethanol or butanol, in the presence of a base such as triethylamine. An alkali metal alcoholate or trialkylsilanolate can also be used in a direct reaction with the chlorophosphite.

Step 2 involves reacting an aryl aldehyde or heteroarylaldehyde with an alcohol, $R^3OH$, to give the corresponding aryl aldehyde acetal. The aryl aldehyde can be a benzaldehyde, a naphthaldehyde, an anthraldehyde and the like. The $R^2$ substituent on the aryl aldehyde, preferably positioned meta to the point of attachment of the aldehydic group in the benzaldehydes illustrated above, can be an oxygen-linked functional group, e.g., an ester group such as pivaloyloxy, acetoxy and the like, an ether group such as methoxy, benzyloxy, and the like, a nitro group, a halogen atom, or hydrogen (see Tables 2–6 in the above-mentioned copending application). Functional group $X^1$ in the aryl aldehyde may be located ortho, meta or para to the point of attachment of the aldehydic group to the aryl ring, and can be a lower alkoxy group such as methoxy, ethoxy or the like, hydrogen, or an alkyl group (see Table 2 in the above-mentioned copending application). In the alcohol reactant $R^3OH$, $R^3$ can be, for example, a lower alkyl group such as methyl, ethyl and the like, a lower aralkyl group, a lower alkoxy alkyl group, a substituted amino alkyl group, or a substituted siloxy alkyl group (see Tables 2–6 in the above-mentioned copending application). Diols such as ethylene glycol or propylene glycol, e.g., HO—(CH$_2$)$_n$—OH, produce cyclic acetals which are within the scope of this invention. The acetalization reaction between the aryl aldehyde and the alcohol or diol is carried out in conventional fashion, preferably in the presence of a catalyst, e.g., a Lewis acid, such as hydrochloric acid, p-toluenesulfonic acid or its polyvinylpyridine salt, or Amberlyst XN1010 resin, accompanied by removal of water. Water can be removed using, e.g., trialkylorthoformate, 2,2-dialkoxypropane, anhydrous copper sulfate, or a molecular sieve, or by azeotropic distillation in, for example, a Dean-Stark apparatus. In cases in which acetalization may proceed with poor conversion or yield, it is possible to use the Noyori reaction wherein any of the aforementioned alcohols (R$^3$OH) or diols are reacted with the aldehyde as their mono or bis trialkylsilyl ethers in the presence of trimethylsilyl triflate as catalyst in a chlorinated hydrocarbon solvent.

Step 3 involves reacting the tertiary phosphorous acid alkyl ester (trialkylphosphite) produced in Step 1 with the aryl aldehyde dialkyl or cyclic acetal produced in Step 2, preferably in the presence of at least one equivalent of a Lewis acid catalyst such as BF$_3$ etherate or the like, to give the corresponding phosphonate, essentially according to Burkhouse, et al., *Synthesis*, 330 (1984). Aryl aldehyde dialkyl acetals react with between 1 and 1.5 equivalents of a trialkylphosphite in the presence of a Lewis acid in an organic solvent such as methylene chloride, under an inert atmosphere, e.g., argon gas, at temperatures below 0° C., to produce in almost quantitative yields the corresponding 1-alkoxy-1-arylmethane phosphonate esters. The phosphonates are generally oils that can be used directly or purified by chromatography on silica gel or by distillation in Vacuo. $^1$HNMR spectra will exhibit a doublet near 4.7 ppm (J=15.5 Hz) due to the benzylic proton, split by the adjacent phosphorous anion; occasionally, two doublets of unequal intensity will be observed.

In step 4, the phosphonate-stabilized carbanion is used to synthesize olefins by the Horner-Emmons reaction. Specifically, in Step 4.1 a phosphonate-stabilized carbanion is produced from a dialkyl 1-alkoxy-1-arylmethane phosphonate in the presence of a base such as sodium hydride, a sodium amide, a lithium dialkyl amide such as lithium diisopropylamide (LDA), a metal alkoxide, or, preferably, n-butyllithium, in a suitable solvent, preferably in the presence of a slight excess of base, e.g., about 1.05 equivalents for each ionizable group present. Suitable solvents for the reaction can have an appreciable range of polarities, and include, for example, aliphatic hydrocarbons such as hexanes, aromatic hydrocarbons such as benzene, toluene and xylene, ethers such as tetrahydrofuran (THF) or glymes, alkanols such as ethanol and propanol, dimethylformamide (DMF), dimethylacetamide, and dimethylsulfoxide, and the like, or mixtures of these solvents. As lithiophosphonates are insoluble in diethylether, but soluble in ethers such as THF, reactions using LDA or n-butyllithium are preferably run in dry THF/hexane mixtures. It is also preferred to carry out the reaction in an inert atmosphere, e.g., under argon gas. At temperatures below 0° C., the reaction of n-butyllithium with phosphonates proceeds rapidly, as indicated by the instantaneous formation of a dark yellow to burgundy colored solution, depending upon the particular phosphonate used and its concentration.

In Step 4.2, the phosphonate-stabilized carbanion is reacted, preferably in molar excess, with a carbonyl compound T=O. When T=O is a substituted or unsubstituted adamantanone, e.g., adamantanone itself, the reaction begins immediately upon addition of the ketone, preferably from about 0.8 to about 0.95 equivalents of the ketone, to the stabilized carbanion, and goes to completion under reflux conditions in from about 2 to about 24 hours. Optimization of the T=O equivalency in each case allows complete conversion of this expensive component.

In Step 5 the enol ether is oxidized. Oxidation is preferably accomplished photochemically by treating the enol ether with singlet oxygen ($^1$O$_2$) to add oxygen across the double bond and create the 1,2-dioxetane ring. Photochemical oxidation is preferably carried out in a halogenated solvent such as methylene chloride or the like. $^1$O$_2$ can be generated using a photosensitizer, such as polymer bound Rose Bengal (Hydron Labs, New Brunswick, N.J.) and methylene blue or 5, 10, 15, 20-tetraphenyl-21H,23H-porphine (TPP). Chemical methods of dioxetane formation, using triethylsilylhydrotrioxide, phosphite ozonides, or triarylamine radical, radical cation mediated one-electron oxidation in the presence of $^3$O$_2$, can also be utilized.

When the oxygen-linked functional group R$^2$ on the aryl ring of the enol ether is an alkoxy group or pivaloyloxy group, it can be converted to an enzyme-cleavable group such as a phosphate group, an acetoxy group, an O-hexopyranoside group, or the like, by carrying out the following additional steps, involving the enol ether produced in Step 4 of the foregoing reaction sequence, prior to carrying out the oxidation reaction of Step 5, as shown below:

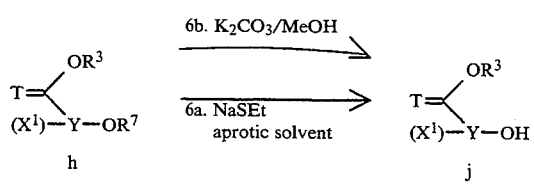

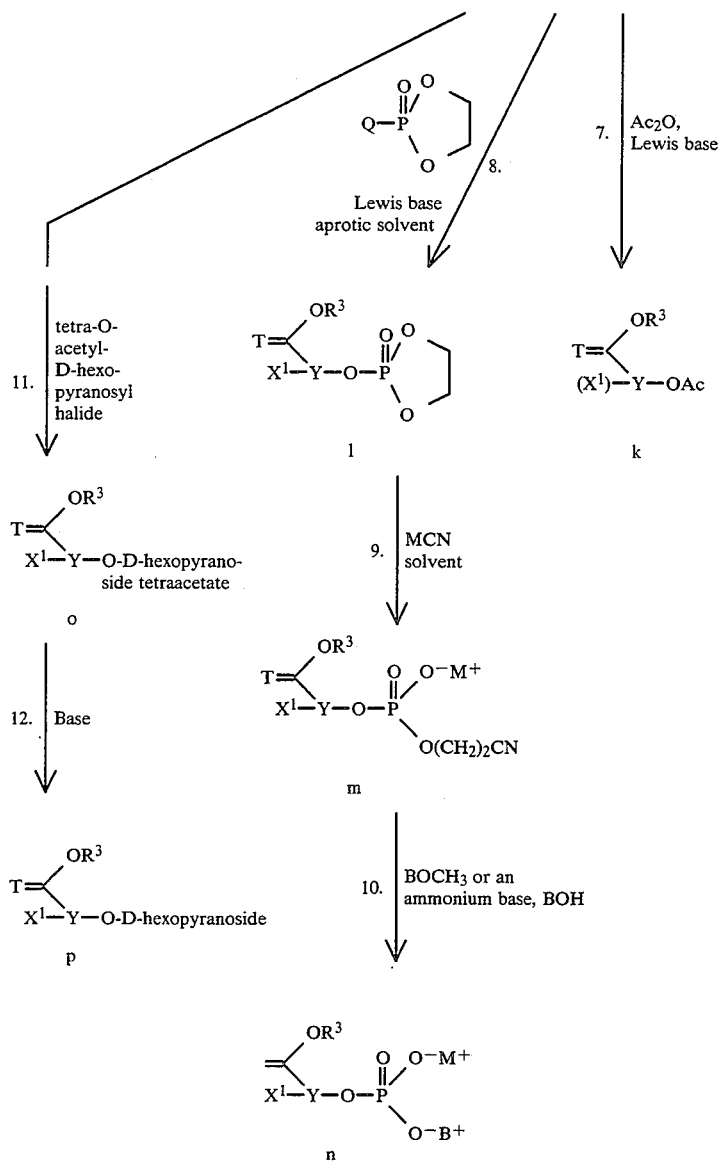

Step 6a involves phenolic ether or thioether cleavage of the $R^7$ substituent (wherein $R^7$ is preferably lower alkyl, e.g., methyl, lower alkenyl, e.g., allyl, or aralkyl, e.g., benzyl), preferably with sodium thioethoxide, in an aprotic solvent such as DMF, NMP, or the like, at temperatures from about 120° C. to about 150° C. Cleavage can also be accomplished with soft nucleophiles such as lithium iodide in refluxing pyridine, sodium cyanide in refluxing DMSO, or sodium monosulfide in refluxing N-methyl-2-pyrrolidone. When $R^7$ is pivaloyl, ester cleavage can be accomplished with NaOMe, KOH or $K_2CO_3$ in an alcoholic solvent such as MeOH at temperatures from about 25° C. to reflux (Step 6b).

Acylation of the phenolic hydroxyl group in the thus-obtained hydroxy compound is carried out in Step 7 by adding a small equivalent excess of an acid halide or anhydride, acetic anhydride, or oxalyl chloride with Lewis base, e.g., triethylamine, in an aprotic solvent.

The substituent Q on the cyclic phosphorohalidate used in Step 8 is an electronegative leaving group such as a halogen. The monovalent cation $M^+$ of the cyanide used in Step 9 can be a metallic or alkali metal cation such as $Na^+$ or $K^+$, or a quaternary ammonium cation. The cation $B^+$ of the ammonium base of Step 10 is an ammonium cation; however, NaOMe can also be used as the base. T, $R^3$ and $X^1$ are as defined above.

Steps 8, 9 and 10 can be performed separately or in a one-pot or two-pot operation. A cyclic phosphorohalidate, e.g., cyclic phosphorochloridate, is preferred for use in Step 8 not only because of its monofunctionality, chemoselectivity and enol ether-compatible deprotection mode of action, but also because it is $10^6$ times more reactive than the corresponding acyclic compounds. In a 3-step, 2-pot operation, the phenolic hydroxyl group in the free hydroxyl product produced in Step 6 is reacted with 2-halo-2-oxo-1,3,2-dioxaphospholane to yield the cyclic phosphate triester (Step 8). This triester is subjected to ring opening with MCN (e.g., NaCN) to yield the corresponding 2-cyanoethyl diester (Step 9). A base, e.g., ammonium hydroxide or sodium methoxide, then provokes a facile β-elimination reaction, yielding a filterable disodium sodium ammonium salt (Step 10). In benzene, THF, diethylether or DMF, phosphate triester formation induced by a Lewis base (e.g., a tertiary amine such as triethylamine) or with a preformed alkali metal salt or the phenolic enolether can be effected with phosphorohalidates over a temperature range of about −30° to about 60° C. Subsequently, if a pure monosodium cyanoethylphosphate ester is desired, the ring cleavage with alkalicyanide (MCN) in DMF or DMSO can be carried out in a narrow temperature range of between about 15° and about 30° C. However, in a one-pot or in situ mode this is not as important, and the temperature range widens to about 60° C. on the high end.

Aryl phosphate disalts can also be made from the aryl alcohol enol ether product of Step 6 using an activated phosphate diester of the general formula:

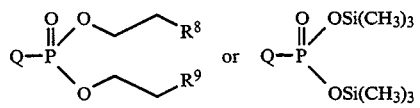

wherein Q is as described above, and $R^8$ and $R^9$ are each independently —CN, —NO$_2$, arylsulfonyl, alkylsulfonyl or trimethylsilyl. Alternatively, the phosphate triester may contain two trimethyl silyl groups, linked to the phosphorous, as shown in the formula above. This reaction can be carried out in the presence of a Lewis base in an aprotic solvent, and yields an aryl phosphate triester. The triester can then be hydrolyzed with a base, M$^+$OH$^-$, M$^+$−OCH$_3$ or M$^+$F$^-$, wherein the cation M$^+$ is an alkali metal, NR$^{10}_4$+ wherein R$^{10}$ is hydrogen or a C$_1$–C$_7$ alkyl, aralkyl, aryl or heterocyclic group, to give the corresponding arylphosphate monoester disalt via $\beta$-elimination or simple hydrolysis. Dioxetane formation by reacting singlet oxygen ($^1$O$_2$) with these enol ether phosphate triesters, followed by similar base-induced deprotection to the dioxetane phosphate monester, may also be carried out.

An alkoxy group on the aryl ring of the enol ether can be converted to a D-sugar molecule linked to the ring via an enzyme cleavable glycosidic linkage by reacting the phenolic precursor in an aprotic organic solvent under an inert atmosphere with a base, such as NaH, and then with a tetra-O-acetyl-phexopyranosyl halide to produce the aryl-O-hexopyranoside tetraacetate (Step 11). The protective acetyl groups can then be hydrolyzed off using a base such as NaOCH$_3$, K$_2$CO$_3$, or NH$_3$ gas, in an alcohol such as methanol, first at 0° C. and then at 25° c for 1 to 10 hours (Step 12), leaving a hexosidase-cleavable D-hexopyranosidyl moiety on the aryl ring.

When the enol ether aryl phosphates are oxidized to bis-quaternary ammonium or corresponding 1,2-dioxetanes (Step 5 above), ion exchange to a bis-quaternary ammonium or monopyridinium salt allows the facile photooxygenation of 0.06M chloroform solutions in the presence of, preferably, methylene blue or TPP, at cold temperatures, e.g., about 5° C. Slower reaction rates and increased photolytic damage to the product may occur with the use of solid phase sensitizers such as polymer-bound Rose Bengal (Sensitox I) or methylene blue on silica gel.

Aryl monoaldehydes or heteroaryl monoaldehydes other than those coming within the formula:

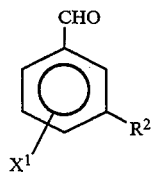

wherein $X^1$ and $R_2$ are as defined above, can also be used as starting materials in carrying out the above-described reaction sequence. Included among such aryl monoaldehydes are the polycyclic aryl monoaldehydes having the formula:

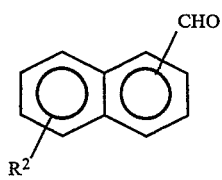

wherein $R^2$ is as defined above and is preferably positioned so that the total number of ring carbon atoms separating the ring carbon atom to which it is attached and the ring carbon atom to which the aldehyde group is attached, including the ring carbon atoms at the points of attachment, is an odd whole number, preferably 5 or greater; see Edwards, et al., U.S. patent application Ser. No. 213,672.

Fused heterocyclic acetals or hemiacetals can also be used as starting materials in carrying out the above-described reaction sequence. Included among such fused heterocyclic acetals are those having the formulas:

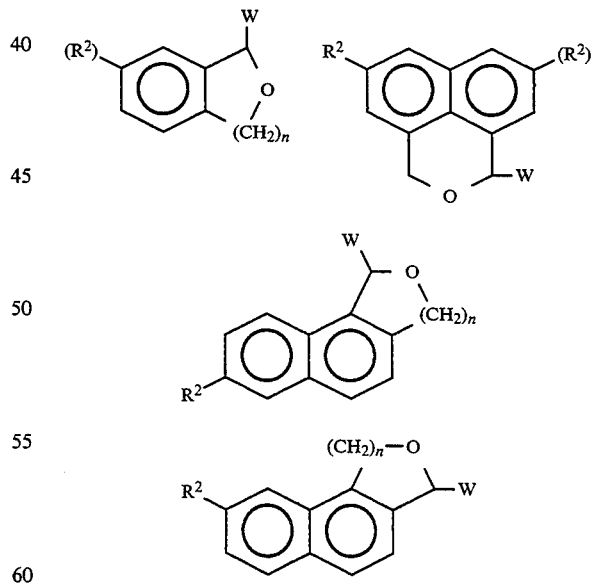

and the like, wherein $R^2$ is as described above, and W can be OR$^3$, wherein R$^3$ is described above, or OH, and n is an integer greater than zero.

Purification of the thus-obtained water-soluble dioxetanes is best achieved at alkaline pH values, e.g., about 7.5 to about 9.0, using reverse phase HPLC with an acetonitrile-water gradient, followed by lyophilization of the product; see Edwards et al., U.S. patent application Ser. No. 244,006.

Typical enzymatically-cleavable water-soluble chemiluminescent 1,2-dioxetanes for use in bioassays which can be prepared by the new synthetic method described in the above-mentioned copending application are the 3-(2′-spiroadamantane)-4-methoxy-4-(3″-phosphoryloxy)phenyl-1,2-dioxetane salts represented by the formula:

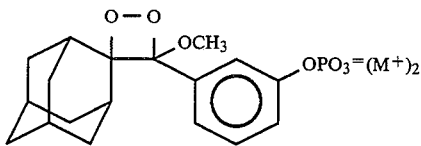

wherein M+ represents a cation such as an alkali metal, e.g. sodium or potassium, or a $C_1$-$C_{18}$ alkyl, aralkyl or aromatic quaternary ammonium cation, $N(R^{10})_4^+$, in which each $R^{10}$ can be alkyl, e.g., methyl or ethyl, aralkyl, e.g., benzyl, or form part of a heterocyclic ring system, e.g., N-methylpyridinium, a fluorescent onium cation, and particularly the disodium salt. A more systematic name for the latter is 3-(4-methoxyspiro[1,2-dioxetane-3,2′-tricyclo[3.3.1.1$^{3,7}$]decan]4-yl)phenyl-phosphate disodium salt.

SUMMARY OF THE INVENTION

It has now been discovered that it is oftentimes advantageous to conduct the acylation reaction of Step 7 in the above-described reaction sequence, or the phosphorylation reaction of Step 8, or the glycosylation reaction of Step 11, using hydroxyaryl enol ether alkali metal salts:

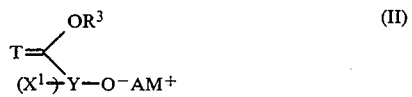

wherein AM+, the alkali metal cation, is lithium, sodium or potassium and T, $R^3$, $X^1$ and Y are as described above, in place of the corresponding free hydroxy compounds depicted as compounds j, the products of Steps 6a and 6b, in this reaction sequence. In certain cases the use of an alkali metal salt of the enol ether rather than the free hydroxy compound results in savings in materials of reaction. For example, acylation of the alkali metal salt of an enol ether by the method of Step 7 above, or phosphorylation of the alkali metal salt by the method of Step 8, preferably proceeds without using a Lewis base in either case. However, as the enol ether is an acid-sensitive functional group, it is sometimes desirable to have present some quantity of a base such as triethylamine or tetramethylethyenediamine, especially where more than one equivalent of an acylation or phosphorylation reagent is being used to force the reaction to completion, and where subsequent exposure to traces of moisture could therefore generate mineral acid which could hydrolyze the enol ether in situ. In other instances there is an actual reduction in reaction steps. Simply employing the reaction conditions described above for Steps 6a and 6b but dispensing with post-reaction protic work-up, for example, will give the enol ether as its alkali metal salt rather than as the free hydroxy compound. Hence, the alkali metal salt need not be obtained by first isolating the free hydroxy compound and then forming the salt in a separate reaction. Instead, the thus-obtained alkali metal salts can be separated by precipitation or used in situ as starting materials for the acylation, phosphorylation or glycosylation reactions.

It is therefore an object of this invention to provide variations in the new synthesis of stable, water-soluble chemiluminescent 1,2-dioxetanes disclosed and claimed in our copending U.S. patent application Ser. No. 402,847.

Another object of this invention is to provide methods for obtaining enol ether alkali metal salt intermediates useful in the acetylation, phosphorylation and glycosylation reactions disclosed and claimed in our copending U.S. patent application Ser. No. 402,847.

A further object of this invention is to provide methods for obtaining and using such enol ether alkali metal salt intermediates that result in savings in materials of reaction, reductions in reaction steps, or both.

These and other objects, as well as the nature, scope and utilization of this invention-, will become readily apparent to those skilled in the art from the following description and the appended claims.

DETAILED DESCRIPTION OF THE INVENTION

Applicants' presently preferred method of providing the enol ether alkali metal salts of this invention involves modification of the step in the above-described reaction sequence, Step 4, in which the Horner-Emmons reaction is used, followed by modification of the subsequent ester cleavage step, Step 6b. Specifically, and as described above, in the first part of this modified procedure a dialkyl 1-alkoxy-1-arylmethane phosphonate:

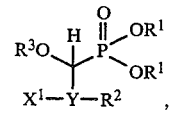

preferably one in which Y is an aryl moiety, e.g, a phenyl ring, $R^2$ is an acyloxy substituent, preferably in the meta-position on the aryl moiety, e.g., a pivaloyloxy group, and $X^1$ can be hydrogen or another of the substituents listed above, is converted to the corresponding phosphonate-stabilized α-carbanion, preferably in solution at low temperature, −20° C. or less, under an inert atmosphere, using an alkali metal-containing base, e.g., from about 1 to about 1.2 equivalents of the alkali metal-containing base, and preferably slightly more than one equivalent of an alkali metal alkylamide such as lithium diisopropylamide or an alkali metal alkyl compound such as n-butyllithium.

Once the α-carbanion is formed the polycyclic ketone T=O is added to the reaction mixture at low temperature, preferably in slightly less than molar excess, then brought to reflux temperature and refluxed for from about 2 to about 24 hours to give a reaction mixture which can include, inter alia, the dialkyl 1-alkoxy-1-arylmethane phosphonate starting material as its anion, its $R^2$ deesterified dianion, or its decomposition products, the hydroxyaryl enol ether alkali metal salt, and the $R^2$ esterified aryl enol ether, the latter particularly being present when the phosphonate starting material includes an aryloxy-substituted aryl moiety (Y—$R^2$) whose acyloxy substituent ($R^2$) has an acyl group that is a good hydroxy protecting group that remains substantially intact during this reaction, e.g., a pivaloyl group ($R^2$=pivaloxyloxy), It has been found, in fact, that when the phosphonate starting material's Y—$R^2$ substituents constitute a pivaloyloxyphenyl group, only about 10–20 percent of the total enol ether product obtained is present as the deesterified enol ether alkali metal salt.

Mild protic work-up of this reaction mixture to separate the desired $R^2$ esterified aryl enol ether (as described, e.g., in Example 7 of our copending application Ser. No. 402,847) is complicated by the presence of several other useful components, all which should, if possible, be recovered in fashion to reduce costs. The $R^2$ esterified aryl enol ether where $R^2$ is a pivaloyloxy group, for example, is a high $R_f$, early eluting product when subjected to column chromatography, while the corresponding hydroxyaryl (deesterified) compound, which is produced during protic work-up to form the hydroxyaryl enol ether lithium salt, and the phosphonate starting material and its decomposition products, are somewhat lower $R_f$ materials, making for a difficultly separable mixture which yields somewhat impure fractions on a large synthetic scale.

Reesterification of the crude, post-reflux Horner-Emmons reaction mixture, however, to substantially esterify the hydroxyaryl enol ether alkali metal salt, preferably using an acid chloride or acid anhydride, e.g., pivaloyl chloride, in at least a molar equivalent amount to the total amount of all aryloxide alkali metal salt present, permits facile separation of the esterified aryl enol ether in near quantitative yield without the above-mentioned complications during chromatography because the hydroxyaryl enol ether is absent after protic workup.

The minimum quantity of acid halide or anhydride to consume the hydroxyaryl alkali metal salt is added in several aliquots to the crude reaction mixture, at a temperature between about 0° C. and about 50° C., over a period of from about 2 to about 24 hours, using thin layer chromatography to monitor the completeness of the reaction. Where $R^2$ is a pivaloyloxy group one gets a much cleaner product, isolated from the reesterified mixture as a crystalline solid using standard techniques, such as recrystallization from hexanes. The mother liquors, uncontaminated with free hydroxyaryl enol ether, are easily plug chromatographed on a large scale, again due to the absence of hydroxyaryl enol ether byproduct.

The final reaction in this preferred method of providing enol ether alkali metal salts involves carrying out ester cleavage to give, instead of the free hydroxy aryl enol ether obtained as in Step 6b of the reaction sequence set out supra, the corresponding alkali metal salt. The salt-forming reaction is preferably carried out using about one molar equivalent of an alkali metal alkoxide, e.g., sodium methoxide, in a lower alkanol, e.g., methanol or enthanol, under anhydrous conditions, i.e., in the presence of as low an amount of moisture as can practicably be achieved, for from about 1 to about 4 hours at room temperature (about 25° C.), followed by removal of the volatiles from the reaction mixture in vacuo (1 mm Hg) with heating at from about 35° C. to about 65° C. for about 24 hours to give the hydroxyaryl enol ether alkali metal salt as a dry solid, directly usable in an acylation, phosphorylation or glycosylation reaction. For example, the free hydroxy enol ether starting material of Example 106 in our copending application Ser. No. 402,847—3-(methoxytricyclo[3.3.1.1$^{3,7}$]dec-2-ylidenemethyl) phenol—can be replaced with its sodium salt—sodium 3-(methoxytricyclo[3.3.1.1$^{3,7}$]dec-2-ylidenemethyl)phenoxide—in a one pot reaction with between about 1 and 1.2 equivalents of 2-chloro-2-oxo-1,3,2-dioxaphospholane in anhydrous dimethylformamide or dimethylsulfoxide to give the corresponding cyclic triester. This triester readily undergoes ring opening with sodium methoxide, and $\beta$-elimination with sodium hydroxide or ammonium hydroxide to give the phosphate monoester salt.

Alternatively, the same reaction can be carried out in a halogenated solvent, e.g., methylene chloride, a polar solvent, e.g., acetonitrile, or an ether or polyether solvent, tetrahydrofuran or diglyme, in the presence, if desired, of hexamethylphosphoramide or a phase transfer catalyst such as tetrabutylammonium bisulfate, with the remaining ring opening and $\beta$-elimination steps being run in dimethylformamide or dimethylsulfoxide. These same procedures can also be used when reacting the enol ether alkali metal salt with the other phosphorylating agents listed above, except that the $\beta$-elimination or hydrolysis reactions can be run immediately following triester formation.

The enol ether alkali metal salts of this invention can be obtained by yet another modification in the above-described reaction sequence, this time to Step 4 alone. A dialkyl 1-alkoxy-1-arylmethane phosphonate, Formula d above, whose aryl moiety (Y) has an acyloxy substituent ($R^2$) the acyl group of which is a poor hydroxy protecting group, i.e., one that will be substantially cleaved during this reaction, such as an acetyl group or the like, can be reacted with three equivalents of a lithium alkyl compound, e.g., n-butyllithium, in solution under an inert atmosphere at low temperature, $-20°$ C. or less, to give the corresponding phosphonate-stabilized $\alpha$-carbanion as its lithio salt. Addition of the polycyclic ketone T=O, preferably in less than a molar equivalent quantity, to the reaction mixture, followed by refluxing for from about 2 to about 24 hours, gives the lithio salt of the hydroxyaryl enol ether directly.

Similarly, phenolic ether or thioether cleavage of the $R^7$ substituent exactly as described for Step 6a in the above-described reaction sequence, using an alkali metal-containing reagent, initially yields the corresponding hydroxyaryl or mercaptoaryl alkali metal salt. Instead of subjecting the thus-obtained reaction mixture to protic work-up, the thus obtained salt can be separated by precipitation at 0° C., preferably in the presence of a nonsolvent such as an ether, e.g., diethyl ether, or used in situ to accomplish direct acylation, phosphorylation or glycosylation in the manner described in Steps 7, 8 and 11 of the above-described reaction sequence.

The conditions under which the hydroxyaryl enol ether alkali metal salts of this invention can be subjected to acylation, phosphorylation or glycosylation are as described in our copending application Ser. No. 402,847, except that any of the solvents mentioned above, e.g., dimethylformamide or tetrahydrofuran, or mixtures of these solvents, are used for the reaction with the acylating, phosphorylating or glycosylating reagent over a temperature range of about 0° C. to about 60° C., preferably in the absence of a Lewis base, with any remaining process steps being identical to those in our copending application.

In order that those skilled in the art can more fully understand this invention, the following examples are set forth. These examples are given solely for purposes of illustration, and should not be considered as expressing limitations unless so set forth in the appended claims.

EXAMPLE I

Diethyl 1-methoxy-1-(3-pivaloyloxyphenyl)methane phosphonate (65.8 g, 0.184 mol.), prepared as described in our copending application Ser. No. 402,847, was placed in a dry 1 liter flask under argon. Dry tetrahydrofuran (165 ml.) was added, followed by 2-adamantanone (24.8 g, 0.165 mol.). The solution was stirred to homogeneity and set aside. In a separate 500 ml. flask, n-butyllithium (81 ml. of a 2.5M solution in hexanes) was added from a dropping funnel to a solution of diisopropylamine (30 ml., 0.214 mol.) in 200 ml. of tetrahydrofuran, which had been cooled in a dry ice-acetone bath to $-78°$ C. under an argon atmosphere. The resulting solution of lithium diisopropylamide was stirred at low temperature for another 25 minutes and then cannulated with a double tipped needle into the solution of phosphonate and 2-adamantanone which had also been cooled to $-78°$ C. Lithium diisopropylamide was thus added dropwise, with vigorous stirring, over a 1.5 hour period. The clear, light brown reaction mixture was then stirred for an additional 30 minutes at low temperature, warmed to room temperature, and then refluxed for 2.5 hours under argon and cooled to room temperature. Thin layer chromatography (TLC) of the crude reaction mixture (Whatman $K_5F$; 10% ethyl acetate-hexanes) displayed three U.V. absorbing spots; one at the origin, one at $R_f.28$, and the major spot at $R_f.70$.

The thus-obtained reaction mixture was treated with several aliquots of pivaloyl chloride, with stirring for several hours at room temperature between additions. After a total of 4.75 ml. (38.5 mmol.) of the acid chloride had been added. TLC showed that the spot at $R_f.28$ had completely disappeared. Thus, the lithium salt of methoxy(3-hydroxyphenyl)methylene adamantane present in the reaction mixture had been converted to the corresponding pivaloate ester at $R_f.70$. Tetrahydrofuran was then partially removed by distillation at atmospheric pressure to obtain a thick slurry, which was then partitioned between water and 10% ethyl acetate-hexanes. The aqueous layer was separated and washed again three times with the same solvent. The combined organics were then washed several times with a saturated aqueous solution of sodium bicarbonate, dried over sodium sulfate, and filtered to remove any particulates. Concentration of the solution on a rotory evaporator gave a thick slurry of crystalline product. The slurry was diluted with hexanes, cooled to $-20°$, and filtered. The filter cake was washed under argon with hexanes which had been cooled in a dry ice-acetone bath. The orange-brown filtrate was concentrated to an oil, which was dissolved in minimal hexanes, seeded with crop 1 and cooled to yield a second crop of the product. The mother liquors from this operation were then plug chromatographed on 74 g. of silica gel, eluting with hexanes to leave the origin material (residual phosphonate ester and its decomposition products) behind. A third crop of product could then be obtained upon concentration of the eluant. The total yield of methoxy(3-pivaloyloxyphenyl) methylene adamantane was 54.67 g (79%), melting point 83°–85°. Spectral data (1R, and $^1$HNMR) were identical to those previously reported in our copending application Ser. No. 402,847; see Example 59.

EXAMPLE II

A flame-dried flask was charged with methoxy(3-pivaloyloxyphenyl)methylene adamantane (5.01 g, 14.1 mmol.). Anhydrous methanol (40 ml.) was added under argon. The resulting suspension was stirred vigorously during the dropwise addition of 4.37M sodium methoxide in methanol (3.25 ml., 14.2 mmol.). The suspended solid dissolved during this operation. After stirring the mixture for one hour at room temperature, TLC (Whatman $K_5F$; 10% ethyl acetate-hexanes) showed that a very faint trace of the starting material remained ($R_f.70$). One drop of the sodium methoxide solution was added to the clear solution, which was then concentrated on a rotory evaporator (bath temperature 35°) and then pumped in vacuo (1.0 mm. Hg) at 40° for 24 hours. The 15 resulting dry, white solid, sodium 3-(methoxytricyclo [3.3.1.1$^{3,7}$]dec-2-ylidenemethyl)phenoxide, weighed 4.1 g. (quantitative yield). It was insoluble in dichloromethane, and TLC of the supernate showed no evidence for the presence of any phenolic impurities. A nujol mull of the product displayed an 20 infrared spectrum which was devoid of OH stretch absorbances between 3500 and 3300 cm$^{-1}$. The phenolate salt did not exhibit a melting point below 280°, but did darken somewhat beginning at 170°. It was kept dry during all subsequent manipulations, and stored in a dessicator over Drierite.

IR (nujol mull): 1572, 1405, 1310, 1285, 1198, 1175, 1150, 1090, 988, 870, 800, 777 cm$^{-1}$.

EXAMPLE III

Sodium 3-(methoxytricyclo[3.3.1.1$^{3,7}$]dec-2-ylidenemethyl)phenoxide (1.74 g., 6.0 mmol.) was added under argon to 10 ml. of scrupulously dried dimethylformamide containing several drops of triethylamine. The resulting slurry was vigorously swirled during the addition of 2-chloro-2-oxo-1,3,2-dioxaphospholane (0.580 ml., 6.3 mmol.) over 25 minutes. The mixture thinned considerably during this addition and over an additional 3.5 hours of vigorous stirring at room temperature. Dry sodium cyanide (0.325 g. 6.6 mmol.) was then added, with exclusion of moisture, and stirring was continued overnight at room temperature to give an orange, cloudy solution. The solvent was removed in vacuo (1.0 mm Hg) at 50° and the residue was chased twice with o-xylenes to further eliminate DMF.

The resulting brown foam was dissolved in 10 ml. of methanol prior to the dropwise addition of 4.37M sodium methoxide in methanol (1.30 ml., 5.7 mmol.). After 30 minutes, the solvent was removed on the rotory evaporator and the residue was slurred in 5% water-/acetone (v/v) and filtered. The solid filter cake was dissolved in water and subjected to reverse phase chromatography (PLRP polystyrene preparative HPLC column, using a water-acetonitrile gradient) to conveniently isolate disodium 3-(methoxytricyclo[3.3.1.1$^{3,7}$]-dec-2-ylidenemethyl)phenyl phosphate in good yield as a white fluffy solid after lyophilization of the appropriate fractions. The $^1$HNMR spectral data for the product were identical to those reported in copending application Ser. No. 402,847.

The above discussion of this invention is directed primarily to preferred embodiments and practices thereof. It will be readily apparent to those skilled in this art that further changes and modifications in the actual implementation of the concepts described herein can easily be made without departing from the spirit and scope of the invention as defined by the following claims.

We claim:

1. A process for preparing a mercaptoaryl or a hydroxyaryl enol ether alkali metal salt having the formula:

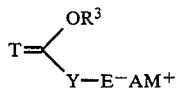

in which T is a substituted or unsubstituted adamant-2-ylidene group, $OR^3$ is an ether group, Y is a light-emitting fluorophore-forming group which will be part of a luminescent substance formed by decomposition of a 1,2-dioxetane subsequently formed from the hydroxyaryl enol ether alkali metal salt, capable of absorbing energy to form an excited state from which it emits optically detectable energy to return to its ground state, E is oxygen or sulfur, and $AM^+$ is an alkali metal cation, which comprises subjecting the corresponding etherified or thioetherified aryl enol ether having the formula:

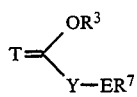

in which $R^7$ is a substituted or unsubstituted alkyl, alkenyl or aralkyl group, to ether cleavage with an alkali metal-containing reagent to give the corresponding hydroxyaryl enol ether alkali metal salt or mercaptoaryl enol ether alkali metal salt.

2. A process as described in claim 1 wherein the alkali metal-containing reagent is sodium thioethoxide, lithium iodide, sodium cyanide or sodium monosulfide.

3. A process as described in claim 2 wherein $R^7$ is methyl, E is oxygen, and the hydroxyaryl enol ether alkali metal salt is recovered by precipitation at 0° C.

4. A process as described in claim 3 wherein $R^3$ is methyl and Y is phenyl.

5. A process for preparing a hydroxyaryl enol ether alkali metal salt having the formula:

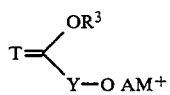

in which T is a substituted or unsubstituted adamant-2-ylidene group, $OR^3$ is an ether group, Y is a light-emitting fluorophore-forming group which will be part of a luminescent substance formed by decomposition of a 1,2-dioxetane subsequently formed from the hydroxyaryl enol ether alkali metal salt, capable of absorbing energy to form an excited state from which it emits optically detectable energy to return to its ground state, and $AM^+$ is an alkali metal cation, which comprises the step of carrying out ester cleavage with an alkali metal alkoxide in a lower alkanol on an esterified aryl enol ether having the formula:

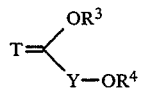

in which $R^4$ is a pivaloyl group, under anhydrous conditions to give the hydroxyaryl enol ether alkali metal salt.

6. A process as described in claim 5, wherein the alkali metal alkoxide and lower alkanol are sodium methoxide and methanol, respectively.

7. A process as described in claims 5 or 6, wherein $R^3$ is methyl and Y is phenyl.

8. A process as described in claim 3, wherein the salt is recovered by precipitation at 0° C. in the presence of a nonsolvent.

9. A process for preparing a hydroxyaryl enol ether lithio salt having the formula:

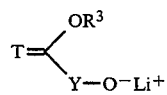

in which T is a fused, substituted or unsubstituted polycycloalkylidene group, $OR^3$ is an ether group, and Y is a light-emitting fluorophore-forming group which will be part of a luminescent substance formed by decomposition of a 1,2-dioxetane subsequently formed from the hydroxyaryl enol ether alkali metal salt, capable of absorbing energy to form an excited state from which it emits optically detectable energy to return to its ground state, which comprises (1) reacting a corresponding dialkyl 1-alkoxy-1-arylmethane phosphonate having the formula:

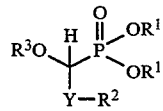

in which $R_1$ is an alkyl group and $R_2$ is a hydroxy protecting acyl group that will be substantially cleaved during the reaction, with three equivalents of a lithium alkyl compound in solution at low temperature under an inert atmosphere, and (2) adding to the resulting mixture containing the corresponding phosphonate-stabilized α-carbanion a ketone having the formula T=O and reacting to give the hydroxyaryl enol ether lithio salt.

10. A process as described in claim 9 wherein step (1) is carried out at a temperature of −20° C. or less and step (2) is carried out from low temperature to reflux using slightly less than a molar excess of the ketone T=O.

11. A process as described in claim 10 wherein $R^2$ is an acetyl group and the lithium alkyl compound used in step (1) is n-butyllithium.

12. A process as described in claim 10 wherein the dialkyl 1-alkoxy-1-arylmethane phosphonate is diethyl 1-methoxy-1-(3-acetoxyphenyl)methane phosphonate.

13. A process as described in claims 11 or 12 wherein the ketone T=O is 2-adamantanone.

* * * * *